United States Patent [19]
Aloup et al.

[11] Patent Number: 4,751,234
[45] Date of Patent: Jun. 14, 1988

[54] CERTAIN N-ALKYL-2-[(QUINOLIN-3-YL)-TETRAHYDRO-PYRAN OR FURAN]-2-CARBOTHIAMIDE 1-OXIDE DERIVATIVES USEFUL FOR TREATING HYPERTENSION

[75] Inventors: Jean-Claude Aloup, Villeneuve-le-Roi; Jean Bouchaudon, Morsang sur Orge; Daniel Farge, Thiais; Claude James, Paris, all of France

[73] Assignee: Rhone-Poulenc Sante, Courbevoie, France

[21] Appl. No.: 766,199

[22] Filed: Aug. 16, 1985

Related U.S. Application Data

[62] Division of Ser. No. 504,789, Jun. 16, 1983, Pat. No. 4,568,682.

[30] Foreign Application Priority Data

Jun. 17, 1982 [FR] France .................. 82 10614

[51] Int. Cl.⁴ ............... C07D 215/60; C07D 409/09; A61K 31/47
[52] U.S. Cl. ..................... 514/314; 546/175; 546/268; 546/283; 546/284; 514/336
[58] Field of Search ............... 546/175; 514/314

[56] References Cited

U.S. PATENT DOCUMENTS

| | | | |
|---|---|---|---|
| 4,272,534 | 6/1981 | Aloup et al. | 514/229 |
| 4,277,484 | 7/1981 | Rosen | 514/324 |
| 4,379,154 | 5/1981 | Aloup et al. | 514/314 |
| 4,456,758 | 6/1984 | Aloup et al. | 546/284 |
| 4,568,682 | 2/1986 | Aloup et al. | 514/336 |

FOREIGN PATENT DOCUMENTS

| | | | |
|---|---|---|---|
| 0046417 | 2/1982 | European Pat. Off. | 514/336 |
| 0048304 | 4/1983 | European Pat. Off. | 514/336 |
| 2046265A | 11/1980 | United Kingdom | 514/336 |

*Primary Examiner*—Alan L. Rotman
*Attorney, Agent, or Firm*—Stevens, Davis, Miller & Mosher

[57] ABSTRACT

Thioformamide derivatives of the formula:

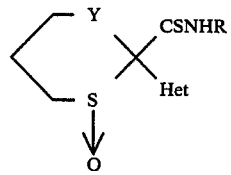

wherein R is hydrogen or alkyl (1 to 4 C), Het is pyridin-3-yl[optionally substituted by alkyl (1 to 4 C) or a halogen], quinolin-3-yl, pyridazin-4-yl, pyrimidin-5-yl, thiazol-5-yl, thieno[2,3-b]pyridin-5-yl or thieno[3,2-b]pyridin-6-yl, and Y is a valency bond or a methylene radical, are new compounds, which are particularly useful as antihypertensive agents.

6 Claims, No Drawings

CERTAIN N-ALKYL-2-[(QUINOLIN-3-YL)-TETRAHYDROPYRAN OR FURAN]-2-CARBOTHIAMIDE 1-OXIDE DERIVATIVES USEFUL FOR TREATING HYPERTENSION

This is a division of application Ser. No. 504,789 filed June 16, 1983, now U.S. Pat. No. 4,568,682 issued Feb. 4, 1986.

This invention relates to new therapeutically useful thioformamide derivatives, to a process for their preparation and to pharmaceutical compositions containing them.

The new thioformamide derivatives of the present invention are those compounds of the general formula:

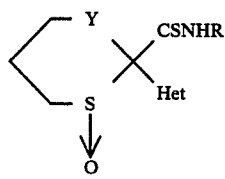
(I)

wherein R represents a hydrogen atom or a straight- or branched-chain alkyl radical containing 1 to 4 (preferably 1 or 2) carbon atoms, Het represents a heterocyclic radical of aromatic character containing one or two nitrogen atoms selected from pyridin-3-yl (optionally substituted by a straight- or branched-chain alkyl radical containing 1 to 4 carbon atoms or by a halogen atom), quinolin-3-yl, pyridazin-4-yl, pyrimidin-5-yl, thiazol-5-yl, thieno[2,3-b]pyridin-5-yl and thieno[3,2-b]pyridin-6-yl, and Y represents a valency bond or a methylene radical.

The presence of an oxygen atom on the ring sulphur atom creates an asymmetry in the molecule which, in association with the adjacent asymmetric carbon atom, leads to 4 stereoisomers which, optionally, can be separated into two racemic pairs designated hereafter by "A Form" or "the more polar product", and "B Form" or "the less polar product" [the polarity being determined by thin layer chromatography (TLC)]. These forms can themselves be resolved. It is understood that the present invention relates to all the stereoisomeric forms and mixtures thereof.

According to a feature of the invention, the thioformamide derivatives of general formula (I) are prepared by the process which comprises reacting ammonia or an amine of the general formula:

R—NH₂ (II)

(wherein R is as hereinbefore defined) with a dithioester of the general formula:

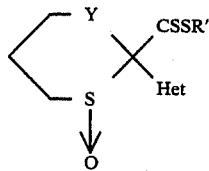
(III)

wherein the symbols Het and Y are as hereinbefore defined, and R' represents a straight- or branched-chain alkyl radical containing 1 to 4 carbon atoms, or a benzyl or carboxymethyl radical, and then optionally separating the A and B forms of the thioformamide derivative obtained.

In general, the reaction is carried out with an excess of ammonia or of an amine of general formula (II), without a solvent or in an organic solvent such as an aromatic hydrocarbon, an ether or an alcohol of low molecular weight, or a mixture of these solvents, at a temperature between 20° and 130° C., optionally under pressure.

It is particularly advantageous for the thiol formed during the reaction to be fixed in the form of a heavy metal salt using a thiol acceptor such as mercuric chloride.

The A and B forms can be separated by crystallisation or by chromatography of the mixture obtained.

The dithioester sulphoxides of general formula (III) can be obtained by the following methods:

(1) By reaction of a strong base with a heterocyclic compound of the general formula:

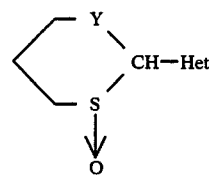
(IV)

(wherein Het and Y are as hereinbefore defined), followed by reacting the resulting product with carbon disulphide and then with a compound of the general formula:

R'—Z (V)

wherein R' is as hereinbefore defined, and Z represents a halogen atom, preferably a chlorine, bromine or iodine atom, or a reactive ester radical, preferably a mesyloxy or tosyloxy radical.

The reaction is generally carried out in an ether such as tetrahydrofuran, to which hexamethylphosphoramide has generally been added, to a temperature between −20° and +50° C.

It is particularly advantageous to employ potassium tert.-butoxide as the strong base.

The products of general formula (III) thus obtained are in the form of a mixture of sulphoxides of different stereochemical forms, the relative percentage of which varies according to the nature of Y; when Y represents a valency bond, the sulphoxide of general formula (III) exists essentially in the form which, when treated with ammonia or an amine of general formula (II), leads to the B form (the less polar form) of the thioamide of the general formula (I); when Y represents a methylene radical, the sulphoxide of general formula (III) exists essentially in the form which, when treated with ammonia or an amine of general formula (II), leads to the A form (the more polar form) of the thioamide of the general formula (I).

The heterocyclic compounds of general formula (IV) can be prepared by one of the following methods:

(a) By the cyclisation of a compound of the general formula:

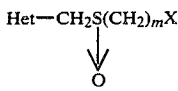  (VI)

wherein Het is as hereinbefore defined, m represents 3 or 4 and X represents a halogen atom, preferably a chlorine or bromine atom, or a reactive ester radical, preferably a mesyloxy or tosyloxy radical.

The reaction is generally carried out in an anhydrous organic solvent such as tetrahydrofuran or hexamethylphosphoramide, or a mixture of these solvents, at a temperature between $-20°$ and $+50°$ C., in the presence of an organic base such as potassium tert.-butoxide.

In practice, it is possible to prepare the dithioester of general formula (III) from the product of the general formula (VI) without isolating the product of the general formula (IV). In this case, the product of the general formula (VI) is cyclised under the conditions indicated above, at least two equivalents of potassium tert.-butoxide being used, and the carbon disulphide and the compound of general formula (V) are then added to the reaction mixture following the procedure indicated above.

The compounds of general formula (VI) can be obtained by oxidising a sulphide of the general formula:

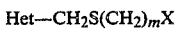  (VII)

wherein Het is as hereinbefore defined, m represents 3 or 4 and X represents a halogen atom, preferably a chlorine or bromine atom, or a reactive ester radical, preferably a mesyloxy or tosyloxy radical.

The oxidation is carried out using one equivalent of a reagent commonly used for converting a sulphide to a sulphoxide, the reaction being carried out in a suitable solvent. For example, it is possible to use hydrogen peroxide in acetone or in acetic acid, an alkali metal periodate in an aqueous-organic solvent such as water-/ethanol or water/acetonitrile, or a peroxycarboxylic acid (eg peracetic, perbenzoic, m-chloroperbenzoic, p-nitroperbenzoic or perphthalic acid) in a chlorinated solvent (e.g. methylene chloride or dichloroethane), in acetic acid or in a mixture of these solvents. The reaction is generally carried out at a temperature between $-10°$ and $+30°$ C.

In practice, it is particularly advantageous to use m-chloroperbenzoic acid, the reaction being carried out in methylene chloride at a temperature of about $20°$ C.

The sulphides of general formula (VII) can be obtained by the method described in the European Patent Application published under No. 0046,417.

(b) By the oxidation of a compound of the general formula:

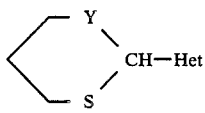  (VIII)

wherein Y and Het are as hereinbefore defined.

The oxidation is carried out under the conditions described above for the preparation of the products of the general formula (VI).

The compounds of general formula (VIII) can be prepared by the method described in the European Patent Application published under No. 0046,417.

(2) By the oxidation of a dithioester of the general formula:

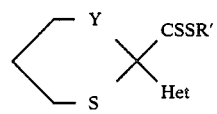  (IX)

wherein the symbols Het, Y and R' are as hereinbefore defined.

The oxidation of the dithioesters of general formula (IX) can be carried out under the conditions described above for the preparation of compounds of general formula (VI).

The dithioester products of general formula (III) thus obtained by process (2) are in the form of a mixture of diastereoisomeric sulphoxides, the relative percentages of which vary between 50-50 and 75-25 according to the nature of the symbols Y, R' and Het.

The dithioester products of general formula (III) obtained by processes (1) and (2) described above can be used either directly in the form of a mixture of the diastereoisomeric forms, or after separation of these forms, to prepare the thioformamide products of general formula (I). The separation of the diastereoisomeric forms of these products can be carried out by fractional crystallisation or, preferably, by chromatography.

The dithioesters of general formula (IX) can be prepared by the method described in the European Patent Application published under No. 0046,417.

The new thioformamide products according to the invention can be purified by the usual physical methods, in particular crystallisation and chromatography.

European Patent Application published under No. 0046,417 has already disclosed the sulphides corresponding to the products of the present invention; the hitherto known sulphides are active as antihypertensive agents.

The new thioformamide derivatives according to the present invention possess improved antihypertensive properties which could not have been predicted from knowledge of the prior art.

At doses of between 0.02 and 50 mg/kg animal body weight, administered orally, they lower the arterial pressure in spontaneously hypertensive rats (SHR) of the OKAMOTO-AOKI strain. The use of spontaneously hypertensive rats for studying antihypertensive products is described by J. L. ROBA, Lab. Anim. Sci., 26, 305 (1976).

Their lethal dose ($LD_{50}$) in mice is generally more than 300 mg/kg animal body weight, administered orally.

As stated previously, the presence of an oxygen atom on the sulphur atom creates an asymmetry in the molecule which, in association with the adjacent asymmetric carbon atoms, leads to four stereoisomers forming 2 racemic pairs designated by "A Form" or "the more polar product", and "B Form" or "the less polar product".

In general, the products of general formula (I) which are in the more polar form are particularly valuable.

Amongst these products of general formula (I) which are in the more polar form, those which are particularly valuable are the ones in which the symbol R represents an alkyl radical containing 1 to 3 carbon atoms, Het represents a pyridin-3-yl or quinolin-3-yl radical and Y represents a methylene radical.

Those which are more particularly valuable are the ones in which the symbol R represents a methyl or ethyl radical, Het represents a pyridin-3-yl or quinolin-3-yl radical and Y represents a methylene radical.

The following products are of outstanding interest:

N-methyl-2-(pyridin-3-yl)tetrahydrothiopyran-2-carbothioamide 1-oxide, A Form (the more polar product), N-ethyl-2-(pyridin-3-yl)tetrahydrothiopyran-2-carbothioamide 1-oxide, A Form (the more polar product), N-methyl-2-(quinolin-3-yl)tetrahydrothiopyran-2-carbothioamide 1-oxide, A Form (the more polar product), and N-methyl-2-(pyridin-3-yl)tetrahydrothiophen-2-carbothioamide 1-oxide, A Form (the more polar product).

The following non-limitative examples illustrate the invention.

EXAMPLE 1

A 33% (weight/volume) solution of methylamine in ethanol (10.2 cc) is added dropwise, in the course of 5 minutes, to a solution of methyl 2-(pyridin-3-yl)tetrahydrothiopyran-2-carbodithioate 1-oxide (a single stereoisomeric form; 10.2 g) in ethanol (150 cc), kept at between 25° and 30° C. The solution is then stirred for 1 hour 35 minutes at a temperature of about 22° C. and a further amount of 33% (weight/volume) solution of methylamine in ethanol (1.5 cc) is then added. After it has been stirred for 1 hour at the same temperature, the reaction mixture is concentrated to dryness under reduced pressure (25 mm Hg; 3.4 kPa) at 40° C. The product obtained (9.8 g) is dissolved in acetonitrile (15 cc) at a temperature of about 20° C. and the solution is kept at a temperature of about 5° C. for 1 hour. The resulting crystals are filtered off, washed twice with acetonitrile (10 cc in total) and dried under reduced pressure (25 mm Hg; 3.4 kPa) at 20° C. The product obtained (3.4. g), to which 0.8 g prepared under the same conditions has been added, is dissolved in boiling acetonitrile (80 cc); the solution is treated with decolourising charcoal (0.1 g) and filtered hot and the filtrate is then cooled at a temperature of about 5° C. for 2 hours. The resulting crystals are filtered off, washed twice with acetonitrile (10 cc in total) and dried under reduced pressure (1 mm Hg; 0.13 kPa) at 60° C. This gives the A form of N-methyl-2-(pyridin-3-yl)tetrahydrothiopyran-2-carbothioamide 1-oxide (3.3 g) melting at 228° C. [Rf=0.22 (chromatography on a thin layer of silica gel; solvent: ethyl acetate/methanol (80/20 by volume)].

The methyl 2-(pyridin-3-yl)tetrahydrothiopyran-2-carbodithioate 1-oxide (a single stereoisomeric form) can be prepared in the following manner:

A solution of 3-(4-chlorobutyl)sulphinylmethylpyridine (16.7 g) in anhydrous tetrahydrofuran (90 cc) is added dropwise, in the course of 20 minutes, to a solution of potassium tert.-butoxide (16.2) in a mixture of anhydrous tetrahydrofuran (90 cc) and anhydrous hexamethylphosphoramide (19 cc), the temperature being kept below 12° C. After stirring for 30 minutes at a temperature of about 10° C., a solution of carbon disulphide (16.5 g) in anhydrous tetrahydrofuran (15 cc) is added dropwise, in the course of 5 minutes, at the same temperature. The mixture is stirred for 10 minutes and a solution of methyl iodide (30.8 g) in anhydrous tetrahydrofuran (15 cc) is then added. The reaction mixture is then stirred for 30 minutes, the temperature being allowed to rise gradually to about 20° C. After the addition of distilled water (500 cc), extraction is carried out 4 times with ethyl acetate (450 cc in total). The organic extracts are combined, washed 4times with distilled water (600 cc in total), dried over anhydrous sodium sulphate and concentrated to dryness under reduced pressure (25 mm Hg; 3.4 kPa) at 40° C. The product obtained (12.6 g) is chromatographed on neutral silica gel (130 g) contained in a column of diameter 3.7 cm. Elution is carred out with mixtures of cyclohexane and ethyl acetate containing an increasing proportion of ethyl acetate, in order to remove the impurities less polar than the expected product [Rf=0.39; chromatography on a thin layer of silica gel; solvent: ethyl acetate/methanol (80/20 by volume)]. Elution is then carried out with pure ethyl acetate, fourteen 300 cc fractions being collected; these are combined and concentrated to dryness under reduced pressure (25 mm Hg; 3.4 kPa) at 40° C.

This gives methyl 2-(pyridin-3-yl)tetrahydrothiopyran-2-carbodithioate 1-oxide (a single stereoisomeric form; 4.4 g) melting at 150° C.

The 3-(4-chlorobutyl)sulphinylmethylpyridine can be prepared in the following manner:

A solution of 85% pure m-chloroperbenzoic acid (107 g) in methylene chloride (900 cc) is added dropwise, in the course of 1 hour 30 minutes, at a temperature of about 20° C., to a solution of 4-chlorobutyl pyridin-3-yl-methyl sulphide (103 g) in methylene chloride (900 cc). After stirring for 17 hours at the same temperature, a 10% (by weight) aqueous solution of sodium bicarbonate (3 liters) is added slowly. The organic solution is decanted and then washed with a 10% solution of sodium bicarbonate (1 liter). The aqueous phases are combined and extracted with methylene chloride (500 cc). The organic extracts are combined and washed twice with distilled water (2 liters in total), dried over anhydrous sodium sulphate and concentrated to dryness under reduced pressure (25 mm Hg; 3.4 kPa) at 35° C. The product obtained (87 g) is chromatographed on neutral silica gel (400 g) contained in a column of diameter 4.7 cm. Elution is carried out with methylene chloride (10 liters), three 1 liters fractions, ten 100 cc fractions and twelve 500 cc fractions being collected successively. Fractions 11 to 25 are combined and concentrated to dryness under reduced pressure (25 mm Hg; 3.4 kPa) at 35° C. to give 3-(4-chlorobutyl)sulphinylmethylpyridine (25.4 g) in the form of an orange oil [Rf=0.22; chromatography on a thin layer of silica gel; solvent: ethyl acetate/methanol (80/20 by volume)].

EXAMPLE 2

Ethylamine (34 g) is added dropwise, in the course of 5 minutes, to a solution of methyl 2-(pyridin-3-yl)tetrahydrothiopyran-2-carbodithioate 1-oxide (10.7 g) in ethanol (120 cc), kept at between 20° and 25° C. The solution is then stirred for 1 hour 30 minutes at the same temperature and then concentrated to dryness under reduced pressure (20 mm Hg; 2.7 kPa) at 50° C. The product obtained (12 g) is chromatographed on neutral silica gel (0.040–0.063 mm; 145 g) contained in a column of diameter 4 cm, under a pressure of 40 kPa. The column is eluted with a mixture of ethyl acetate and methanol (90/10 by volume), one 300 cc fraction and thirty-two 120 cc fractions being collected. Fractions 16 to 33 are combined and concentrated to dryness under reduced pressure (20 mm Hg; 2.7 kPa) at 40° C. The product obtained (4 g) is dissolved in a boiling mixture of methyl ethyl ketone (9 cc) and diisopropyl ether (2 cc); after cooling, the solution is kept at a temperature of about 0° C. for 2 hours. The resulting crystals are filtered off, washed with methyl ethyl ketone (3 cc) and with diisopropyl ether (0.5 cc) and dried under reduced pressure (20 mm Hg; 2.7 kPa) at a temperature of about 20° C. The product obtained (2.6 g), to which 1.2 g prepared under the same condtions in an earlier operation have been added, is dissolved in boiling methyl ethyl ketone (25 cc); the solution is treated with decolourising charcoal (0.2 g) and filtered hot and the filtrate is cooled and kept at a temperature of about 0° C. for 1 hour 30 minutes. The resulting crystals are filtered off, washed with methyl ethyl ketone (6 cc) and dried under reduced pressure (1 mm Hg; 0.13 kPa) at 60° C. This gives the A form of N-ethyl-2-(pyridin-3-yl)tetrahydrothiopyran-2-carbothioamide 1-oxide (3 g) melting initially at about 169° C. and then, after resolidification, at 183° C. [Rf=0.32; chromatography on a thin layer of silica gel; solvent: ethyl acetate/methanol (80/20 by volume)].

EXAMPLE 3

The procedure of Example 2 is followed, but propylamine is used as a starting material; this gives N-propyl-2-(pyridin-3-yl)tetrahydrothiopyran-2-carbothioamide 1-oxide melting at 184° C. [Rf=0.34; chromatography on a thin layer of silica gel; solvent: ethyl acetate/methanol (80/20 by volume)].

EXAMPLE 4

The procedure of Example 2 is followed, but isopropylamine is used as a starting material; this gives N-isopropyl-2-(pyridin-3-yl)tetrahydrothiopyran-2-carbothioamide 1-oxide melting at 209° C. [Rf=0.36; chromatography on a thin layer of silica gel; solvent: ethyl acetate/methanol (80/20 by volume)].

EXAMPLE 5

A 33% (weight/volume) solution of methylamine in ethanol (55 cc) is added dropwise, in the course of 25 minutes, to a solution of methyl 2-(quinolin-3-yl)tetrahydrothiopyran-2-carbodithioate 1-oxide (7.7 g) in ethanol (160 cc), kept at a temperature of about 20° C. The solution is then stirred at the same temperature for 15 hours. The resulting crystals are filtered off, washed with ethanol (10 cc) and then 3 times with diisopropyl ether (45 cc in total) and dried under reduced pressure (0.2 mm Hg; 0.027 kPa) at 50° C. The product obtained (3.8 g), to which 0.95 g prepared under the same conditions in another earlier operation has been added, is dissolved in boiling methanol (600 cc); the solution is treated with decolourising charcoal (4 g) and filtered hot and the filtrate is cooled and then kept at a temperature of about 5° C. for 15 hours. The resulting solid is filtered off, washed 4 times with methanol (80 cc in total) and dried under reduced pressure (0.2 mm Hg; 0.027 kPa) at a temperature of about 60° C. This gives N-methyl-2-(quinolin-3-yl)tetrahydrothiopyran-2-carbothioamide 1-oxide (4.3 g) melting at 280° C. [Rf=0.38; chromatography on a thin layer of silica gel; solvent: ethyl acetate/methanol (80/20 by volume)].

Methyl 2-(quinolin-3-yl)tetrahydrothiopyran-2-carbodithioate 1-oxide can be prepared in the following manner:

A suspension of 2-(quinolin-3-yl)tetrahydrothiopyran 1-oxide (34.5 g) in anhydrous tetrahydrofuran (280 cc) is added dropwise, in the course of 45 minutes, at a temperature of about 20° C., to a solution of potassium tert.-butoxide (34.9 g) in anhydrous tetrahydrofuran (800 cc). The mixture is then stirred at the same temperature for 1 hour; a solution of carbon disulphide (27 g) in anhydrous tetrahydrofuran (60 cc) is then added dropwise, in the course of 15 minutes, at a temperature of −4° C. After stirring for 30 minutes, a solution of methyl iodide (51 g) in anhydrous tetrahydrofuran (60 cc) is added dropwise, in the course of 15 minutes, at the same temperature. The mixture is then stirred for 30 minutes, the temperature being allowed to rise gradually to 12° C. The resulting solid is filtered off, washed with methylene chloride (200 cc) and discarded. The filtrate and the wash liquors are combined and concentrated to dryness under reduced pressure (25 mm Hg; 3.4 kPa) at 45° C. The product obtained (51 g) is dissolved in methylene chloride (250 cc); the solution is washed with distilled water (150 cc), dried over anhydrous magnesium sulphate and poured onto neutral silica gel (0.063–0.200 mm; 770 g) contained in a column of diameter 7 cm. The column is eluted with a mixture of methylene chloride and ethyl acetate (50/50 by volume; 13 liters), 1000 cc fractions being collected. Fractions 9 to 13 are combined and concentrated to dryness under reduced pressure (20 mm Hg; 2.7 kPa) at 40° C. This gives methyl 2-(quinolin-3-yl)tetrahydrothiopyran-2-carbodithioate 1-oxide (7.85 g) melting at 210° C. [Rf=0.39; chromatography on a thin layer of silica gel; solvent: ethyl acetate].

2-(Quinolin-3-yl)tetrahydrothiopyran 1-oxide can be obtained in the following manner:

A solution of 3-(4-chlorobutyl)sulphinylmethylquinoline (58.4 g) in anhydrous tetrahydrofuran (450 cc) is added dropwise, in the course of 1 hour 15 minutes, at a temperature of about 0° C., to a solution of potassium tert.butoxide (44.8 g) in anhydrous tetrahydrofuran (200 cc). The mixture is then stirred for 16 hours, the temperature being allowed to rise to 18° C.; acetic acid (15 cc) is then added dropwise, in the course of 15 minutes, at a temperature of between 2° and 10° C. The resulting solid is filtered off, washed twice with methylene chloride (360 cc in total) and discarded. The filtrate and the wash liquors are combined and concentrated to dryness under reduced pressure (20 mm Hg; 2.7 kPa) at 45° C. The product obtained (51 g) is chromatographed on neutral silica gel (0.063–0.200 mm; 185 g) contained in a column of diameter 6.8 cm. The column is eluted with methylene chloride (200 cc), then ethyl acetate (2200 cc) and finally a mixture of ethyl acetate and methanol (90/10 by volume; 1600 cc), forty 100 cc fractions being collected. Fractions 25 to 40 are combined and concentrated to dryness under reduced pressure (20 mm Hg; 2.7 kPa) at 45° C. This gives a mixture of the forms of 2-(quinolin-3-yl)tetrahydrothiopyran 1-oxide (35.8 g) melting at 152° C.–154° C. [Rf=0.09 and 0.17; chromatography on a thin layer of silica gel; solvent: ethyl acetate].

The 3-(4-chlorobutyl)sulphinylmethylquinoline can be prepared in the following manner:

A solution of 82.5% pure m-chloroperbenzoic acid (44.4 g) in methylene chloride (450 cc) is added dropwise, in the course of 1 hour 15 minutes, at a temperature of about 20° C., to a solution of 4-chlorobutyl quinolin-3-ylmethyl sulphide (54.8 g) in methylene chloride (1160 cc). After stirring for 18 hours at the same temperature, an 8% (weight/volume) aqueous solution of sodium bicarbonate (560 cc) is added slowly. The organic solution is decanted, washed with an 8% aqueous solution of sodium bicarbonate (200 cc) and then twice with distilled water (300 cc in total), dried over anhydrous magnesium sulphate and concentrated to dryness under reduced pressure (20 mm Hg; 2.7 kPa) at 45° C. This gives 3-(4-chlorobutyl)sulphinylmethylquinoline (58.1 g) melting at 103° C.

The 4-chlorobutyl quinolin-3-ylmethyl sulphide can be prepared in the following manner:

A 10N aqueous solution of sodium hydroxide (93 cc) is added, in the course of 12 minutes, to a solution of 2-(quinolin-3-ylmethyl)isothiourea dihydrochloride (87 g) in distilled water (200 cc), kept at a temperature of about 0° C. After heating for 20 minutes at a temperature of about 70° C. and then cooling to 12° C., triethylbenzylammonium chloride (3 g) and methylene chloride (125 cc) are added; 1-bromo-4-chlorobutane (51.1 g) is then added dropwise at a temperature of about 4° C., and the stirring is continued for 16 hours at a temperature of about 20° C. The organic phase is separated by decantation and the aqueous phase is extracted twice with methylene chloride (100 cc in total). The organic extracts are combined, washed twice with distilled water (100 cc in total), dried over anhydrous magnesium sulphate and poured onto neutral silica gel (0.063–0.200 mm; 230 g) contained in a column of diameter 4.2 cm. The column is eluted with methylene chloride (1380 cc), one 220 cc fraction being collected, which is discarded, and one 1160 cc fraction being collected, which contains 4-chlorobutyl quinolin-3-ylmethyl sulphide (54.8 g; weight determined by determination of the solution with perchloric acid) and which will be used for the remainder of the synthesis without isolating the product [Rf=0.65; chromatography on a thin layer of silica gel; solvent: ethyl acetate].

The 2-(quinolin-3-ylmethyl)isothiourea dihydrochloride can be prepared as described in the European Patent Application published under No. 0046417.

EXAMPLE 6

A 33% (weight/volume) solution of methylamine in ethanol (2 cc) is added dropwise, in the course of 5 minutes, at a temperature of about 20° C., to a solution of methyl 2-(pyridin-3-yl)tetrahydrothiopyran-2-carbodithioate 1-oxide [the less polar form; Rf=0.13; chromatography on a thin layer of silica gel; solvent: ethyl acetate] (0.35 g) in ethanol (2 cc). After stirring for 2 hours at the same temperature, the reaction mixture is concentrated to dryness under reduced pressure (20 mm Hg; 2.7 kPa) at 30° C. The product obtained (0.28 g) is chromatographed on neutral silica gel (0.040–0.063 mm; 35 g) contained in a column of diameter 2 cm, under a pressure of 40 kPa. Elution is carried out successively with methylene chloride (100 cc), ethyl acetate (100 cc) and a mixture of ethyl acetate and methanol (90/10 by volume; 100 cc), eleven 20 cc fractions being collected. Fractions 6 to 11 are combined and concentrated to dryness under reduced pressure (20 mm Hg; 2.7 kPa) at 40° C. This gives the crude B form, i.e. the less polar form, of N-methyl-2-(pyridin-3-yl)tetrahydrothiopyran-2-carbothioamide 1-oxide (0.22 g) [Rf=0.48; chromatography on a thin layer of silica gel; solvent: ethyl acetate/methanol (80/20 by volume)].

Methyl 2-(pyridin-3-yl)tetrahydrothiopyran-2-carbodithioate 1-oxide can be prepared in the following manner:

A solution of 82.5% pure m-chloroperbenzoic acid (1.25 g) in methylene chloride (10 cc) is added dropwise, in the course of 30 minutes, at a temperature of about 20° C., to a solution of methyl 2-(pyridin-3-yl)tetrahydrothiopyran-2-carbodithioate (1.6 g) in methylene chloride (15 cc). After stirring for 20 hours at the same temperature, the reaction mixture is poured onto neutral silica gel (40 g) contained in a column of diameter 2.6 cm. The column is then eluted successively with methylene chloride (300 cc), a mixture of methylene chloride and ethyl acetate (50/50 by volume; 400 cc) and ethyl acetate (1 liter), one 300 cc fraction, one 400 cc fraction and thirty-nine 25 cc fractions being collected successively.

Fractions 8 to 28 are combined and concentrated to dryness under reduced pressure (15 mm Hg; 2 kPa) at 40° C. This gives the less polar form of methyl 2-(pyridin-3-yl)tetrahydrothiopyran-2-carbodithioate 1-oxide (0.5 g) [Rf=0.13; chromatography on a thin layer of silica gel; solvent: ethyl acetate].

Fractions 30 to 41 are combined and concentrated to dryness under reduced pressure (15 mm Hg; 2 kPa) at 40° C. This gives the more polar form of methyl 2-(pyridin-3-yl)tetrahydrothiopyran-2-carbodithioate 1-oxide (1 g) [Rf=0.07; chromatography on a thin layer of silica gel; solvent: ethyl acetate], which is identical to the dithioester prepared as described in Example 1.

Methyl 2-(pyridin-3-yl)tetrahydrothiopyran-2-carbodithioate can be prepared in the following manner:

A solution of diisopropylamine (7.6 g) in a mixture of anhydrous hexamethylphosphoramide and anhydrous tetrahydrofuran (47/53 by volume; 30 cc) is added dropwise, in the course of 7 minutes, to a 1.6M solution of n-butyllithium in hexane (47 cc), kept under a nitrogen atmosphere and cooled to −61° C. A solution of 4-chlorobutyl pyridin-3-ylmethyl sulphide (6.45 g) in the mixture of anhydrous hexamethylphosphoramide and anhydrous tetrahydrofuran (47/53 by volume; 30 cc) is then added in the course of 10 minutes. After stirring for 1 hour at a temperature of about −60° C., a solution of carbon disulphide (9.1 g) in the mixture of anhydrous hexamethylphosphoramide and anhydrous tetrahydrofuran (47/53 by volume; 30 cc) is added in the course of 10 minutes. After stirring for 10 minutes at the same temperature, a solution of methyl iodide (17 g) in the mixture of anhydrous hexamethylphosphoramide and anhydrous tetrahydrofuran (47/53 by volume; 30 cc) is added in the course of 10 minutes. The reaction mixture is then stirred for 30 minutes at a temperature of about −60° C. and then for 60 minutes, the temperature being allowed to rise gradually to 10° C. After the addition of distilled water (100 cc), the reaction mixture is extracted 5 times with ethyl acetate (400 cc in total). The organic extracts are combined and washed 3 times with distilled water (300 cc in total). After drying over anhydrous sodium sulphate, filtration and concentration to dryness, a brown oil (15.9 g) is obtained which is chromatographed on neutral silica gel (160 g) contained in a column of diameter 3.7 cm. Elution is carried out with cyclohexane (500 cc), a mixture of cyclohexane and ethyl acetate (98/2 by volume; 400 cc), a mixture of cyclohexane and ethyl acetate (95/5 by volume; 400 cc), a mixture of cyclohexane and ethyl acetate (92.8 by volume; 400 cc), a mixture of cyclohexane and ethyl acetate (90/10 by volume; 400 cc) and a mixture of cyclohexane and ethyl acetate (88/12 by volume; 1000 cc), one 500 cc fraction, eight 200 cc fractions and ten 100 cc fractions being collected. Fractions 12 to 19 are combined and concentrated to dryness. This gives methyl 2-(pyridin-3-yl)tetrahydrothiopyran-2-carbodithioate (2.1 g) melting at 90° C.

EXAMPLE 7

A solution of 82.5% pure m-chloroperbenzoic acid (9.8 g) in methylene chloride (130 cc) is added dropwise, in the course of 45 minutes, at a temperature of about 20° C., to a solution of methyl 2-(pyridin-3-yl)tetrahydrothiopyran-2-carbodithioate (12.5 g) in methylene chloride (120 cc). After stirring for 21 hours at the same temperature, the reaction mixture is poured onto neutral silica gel (0.063–0.200 mm; 375 g) contained in a column of diameter 5 cm; the column is then eluted successively with methylene chloride (1 liter), ethyl acetate (600 cc) and a mixture of ethyl acetate and methanol (80/20 by volume; 800 cc), one 1 liter fraction and seven 200 cc fractions being collected. Fractions 5 to 8 are combined and concentrated to dryness under reduced pressure (15 mm Hg; 2 kPa) at 40° C. This gives a mixture of the two forms of methyl 2-(pyridin-3-yl)tetrahydrothiopyran-2-carbodithioate 1-oxide (12.5 g). A 33% (weight/volume) solution of methylamine in ethanol (35 cc) is added dropwise, in the course of 35 minutes, at a temperature of about 20° C., to a solution of the latter mixture (6 g) in ethanol (50 cc). After stirring for 4 hours at the same temperature, the reaction mixture is concentrated to dryness under reduced pressure (20 mm Hg; 2.7 kPa) at 45° C. This gives a crude product (6.2 g) which, in chromatography on a thin later of silica gel, gives two spots corresponding to Rf values of 0.48 and 0.22 [elution solvent: ethyl acetate/methanol (80/20 by volume)]. The two corresponding products are separated in the following manner:

The crude product obtained is dissolved in methylene chloride (55 cc) and the solution is poured onto neutral silica gel (0.040–0.063 mm; 100 g) contained in a column of diameter 2.6 cm; the column is eluted with ethyl acetate (480 cc) under a pressure of 40 kPa, six 80 cc fractions being collected. Fractions 4 to 6 are combined and concentrated to dryness under reduced pressure (15 mm Hg; 2 kPa) at 40 ° C. The product obtained (1.1 g), to which 1.7 g of the same product prepared under the same conditions in an earlier operation have been added, is dissolved in methylene chloride (25 cc); the solution is treated with decolourising charcoal (0.5 g) and filtered and, after the filtrate has been washed 3 times with methylene chloride (15 cc in total), cyclohexane (125 cc) is added and the mixture is then kept at a temperature of about 5° C. for 15 hours. The resulting crystals are filtered off, washed 5 times with cyclohexane (50 cc in total) and dried under reduced pressure (0.1 mm Hg; 0.013 kPa) at 50° C. This gives the B form, i.e. the less polar form, of N-methyl-2-(pyridin-3-yl)tetrahydrothiopyran-2-carbothioamide 1-oxide (1.9 g) melting at 154° C. [Rf=0.48; chromatography on a thin layer of silica gel; solvent: ethyl acetate/methanol (80/20 by volume)].

By continuing the chromatography, it is possible to obtain the A form, i.e. the more polar form [Rf=0.22; chromatography on a thin layer of silica gel; solvent: ethyl acetate/methanol (80/20 by volume)] melting at 228° C.

EXAMPLE 8

Mercuric chloride (2.7 g) and distilled water (5 cc) are added to a solution of methyl 2-(pyridin-3-yl)tetrahydrothiophen-2-carbodithioate 1-oxide (mixture of the two stereoisomeric forms) (2.7 g) in ethanol (25 cc), and a 33% (weight/volume) solution of methylamine in ethanol (5 cc) is then added dropwise, in the course of 10 minutes, at a temperature of about 15° C. The mixture is stirred at the same temperature for 30 minutes; a further amount of the solution of methylamine in ethanol (3 cc) is added. After stirring for 30 minutes, the insoluble material which has appeared is filtered off and the filtrate is concentrated to dryness under reduced pressure (20 mm Hg; 2.7 kPa) at 40° C. This gives a crude product (5 g) which, in chromatography on a thin layer of silica gel, gives two spots corresponding to Rf values of 0.20 and 0.13 [elution solvent: ethyl acetate/methanol (80/20 by volume)]. The corresponding products are separated in the following manner:

Methanol (10 cc) is added to the crude product obtained; the solution is filtered and the filtrate is then poured onto neutral silica gel (0.040–0.063 mm; 75 g) contained in a column of diameter 2.5 cm, and eluted under a pressure of 50 kPa. Elution is carried out successively with a mixture of ethyl acetate and methanol (95/5 by volume; 2040 cc) and then with a mixture of ethyl acetate and methanol (90/10 by volume; 960 cc), 60 cc fractions being collected.

(a) Fractions 19 to 31 are combined and concentrated to dryness under reduced pressure (20 mm Hg; 2.7 kPa) at 40° C. This gives a product (0.7 g) which is purified as follows:

The product is suspended in boiling acetonitrile (15 cc) and the suspension is filtered hot; the filtrate is concentrated to dryness under reduced pressure (20 mm Hg; 2.7 kPa) at 40° C. The product obtained (0.4 g) is dissolved in boiling ethanol (4 cc). After cooling and standing at 0° C. for 30 minutes, the resulting crystals are filtered off, washed twice with ethanol (1 cc in total) and dried under reduced pressure (20 mm Hg; 2.7 kPa) at a temperature of about 20° C. This gives the B form of N-methyl-2-(pyridin-3-yl)tetrahydrothiophen-2-carbothioamide 1-oxide (0.15 g) melting at 158° C. [Rf=0.20; chromatography on a thin layer of silica gel; solvent: ethyl acetate/methanol (80/20 by volume)].

(b) Fractions 38 to 50 are combined and concentrated to dryness under reduced pressure (20 mm Hg; 2.7 kPa); this gives a product (0.65 g) which is purified as follows:

The product is suspended in boiling acetonitrile (12 cc) and the suspension is filtered hot; the filtrate is concentrated to dryness under reduced pressure (20 mm Hg; 2.7 kPa) at 40° C. The product obtained (0.4 g) is dissolved in boiling acetonitrile (2.5 cc). After cooling and standing at 0° C. for 30 minutes, the resulting crystals are filtered off, washed twice with acetonitrile (1 cc in total) and dried under reduced pressure (20 mm Hg; 2.7 kPa) at a temperature of about 0° C. This gives the A form of N-methyl-2-(pyridin-3-yl)tetrahydrothiophen-2-carbothioamide 1-oxide (0.14 g) melting at 204° C. [Rf=0.13; chromatography on a thin layer of silica gel; solvent: ethyl acetate/methanol (80/20 by volume)].

Methyl 2-(pyridin-3-yl)tetrahydrothiophen-2-carbodithioate 1-oxide (mixture of the two stereoisomeric forms) can be prepared in the following manner:

A solution of 85% pure m-chloroperbenzoic acid (8.9 g) in methylene chloride (150 cc) is added dropwise, in the course of 1 hour, at a temperature of about 20° C., to a solution of methyl 2-(pyridin-3-yl)tetrahydrothiophen-2-carbodithioate (11.2 g) in methylene chloride (150 cc). After stirring for 17 hours at the same temperature, the reaction mixture is concentrated to dryness under reduced pressure (20 mm Hg; 2.7 kPa) at 50° C. and the residue is then chromatographed on neutral silica gel (0.040–0.063 mm; 550 g) contained in a column of diameter of 6 cm, under nitrogen pressure (50 kPa). Elution is carried out successively with ethyl acetate (1.2 liters), a mixture of ethyl acetate and methanol (95/5 by volume; 1.2 liters) and a mixture of ethyl acetate and methanol (90/10 by volume; 3.9 liters), one 2.9 liter fraction and thirty-five 100 cc fractions being collected. Fractions 13 to 35 are combined and concentrated to dryness under reduced pressure (20 mm Hg; 2.7 kPa) at 50° C. This gives methyl 2-(pyridin-3-yl)tetrahydrothiophen-2-carbodithioate 1-oxide (10.2 g ) in the form of an orange oil corresponding to a 50/50 mixture of the two stereoisomeric forms [proportion determined by NMR on the resolved proton $H_2$ of the pyridine: $\delta=8.85$ and 8.77 ppm; $J=2.5$ Hz (solvent: $CDCl_3$)] and having a single Rf equal to 0.37 [chromatography on a thin layer of silica gel; solvent: ethyl acetate/methanol (80/20 by volume)].

EXAMPLE 9

A 33% (weight/volume) solution of methylamine in ethanol (15 cc) is added dropwise, in the course of 16 minutes, to a solution of methyl 2-(pyridin-3-yl)tetrahydrothiophene-2-carbodithioate 1-oxide (a single stereoisomeric form) (5.8 g) in ethanol (35 cc), kept at a temperature of about 25° C. After stirring for 1 hour at the same temperature, a further amount of the 33% (weight/volume) solution of methylamine in ethanol (15 cc) is added dropwise, in the course of 10 minutes. After stirring for 50 minutes, the reaction mixture is concentrated to dryness under reduced pressure (20 mm Hg; 2.7 kPa) at 40° C. The product obtained (7.4 g) is chromatographed on neutral silica gel (0.040–0.063 mm; 190 g) contained in a column of diameter of 30 cm. Elution is carried out successively with ethyl acetate (500 cc ), a mixture of ethyl acetate and methanol (97/3 by volume; 1360 cc), a mixture of ethyl acetate and methanol (95/5 by volume; 760 cc) and a mixture of ethyl acatate and methanol (90/10 by volume; 1240 cc), under pressure (50 kPa), five 100 cc fractions and eighty-four 40 cc fractions being collected. Fractions 53 to 89 are combined and concentrated to dryness under reduced pressure (20 mm Hg; 2.7 kPa) at 40° C. The product obtained (1.2 g) is dissolved in boiling ethanol (3.5 cc) and, after cooling and standing at 0° C. for 30 minutes, the resulting crystals are filtered off, washed twice with ethanol (1 cc in total) and dried under reduced pressure (1 mm Hg; 0.13 kPa) at 60° C. This gives N-methyl-2-(pyridin-3-yl)tetrahydrothiophen-2-carbothioamide 1-oxide (B form, i.e. the less polar form) (0.28 g) melting at 156° C. [Rf=0.20; chromatography on a thin layer of silica gel; solvent: ethyl acetate/methanol (80/20 by volume)].

Methyl 2-(pyridin-3-yl)tetrahydrothiophen-2-carbodithioate 1-oxide can be prepared in the following manner:

A solution of 2-(pyridin-3-yl)tetrahydrothiophen-1-oxide (18.1 g) in anhydrous tetrahydrofuran (150 cc) is added dropwise, in the course of 20 minutes, at a temperature of about 20° C., to a solution of potassium tert.-butoxide (14.8 g) in anhydrous tetrahydrofuran (150 cc). After stirring for 40 minutes, a solution of carbon disulphide (14 cc) in anhydrous tetrahydrofuran (100 cc) is added dropwise, in the course of 15 minutes, at −20° C. After stirring for 25 minutes, a solution of methyl iodide (14.5 cc) in anhydrous tetrahydrofuran (100 cc) is added dropwise, in the course of 10 minutes, at the same temperature. The reaction mixture is then stirred for 2 hours 40 minutes, the temperature being allowed to rise gradually to 15° C. The insoluble material which has appeared is filtered off and washed twice with anhydrous tetrahydrofuran (120 cc in total). The filtrate and the wash liquors are combined and concentrated to dryness under reduced pressure (20 mm Hg; 2.7 kPa) at 40° C. The product obtained (25.8 g) is chromatographed on neutral silica gel (0.040–0.063 mm; 500 g) contained in a column of diameter 6 cm. Elution is carried out with a mixture of ethyl acetate and methanol (93/7 by volume; 6.6 liters) under pressure (50 kPa), fourteen 250 cc fractions and thirty-one 100 cc fractions being collected. Fractions 18 to 36 are combined and concentrated to dryness under reduced pressure (20 mm Hg; 2.7 kPa) at 40° C. This gives methyl 2-(pyridin-3-yl)tetrahydrothiophen-2-carbodithioate 1-oxide (5 g) [Rf=0.30; chromatography on a thin layer of silica gel; solvent: ethyl acetate/methanol (80/20 by volume)].

2-(Pyridin-3-yl)tetrahydrothiophene 1-oxide can be prepared in the following manner:

A solution of 85% pure m-chloroperbenzoic acid (76.3 g) in methylene chloride (800 cc) is added dropwise, in the course of 2 hours 10 minutes, at a temperature of about 20° C., to a solution of 2-(pyridin-3-yl)tetrahydrothiophene (62 g) in methylene chloride (650 cc). After stirring for 16 hours at the same temperature, the reaction mixture is concentrated to about a fourth of its initial volume, under reduced pressure, and the concentrate is poured onto neutral silica gel (0.063–0.200 mm; 800 g) contained in a column of diameter 8 cm. Elution is carried out successively with methylene chloride (9 liters) and a mixture of methylene chloride and methanol (95/5 by volume; 7 liters), sixteen 1 liter fractions being collected. Fractions 15 and 16 are combined and concentrated to dryness under reduced pressure (20 mm Hg; 2.7 kPa) at 40° C. The product obtained (54.3 g) is dissolved in methylene chloride (100 cc) and the solution is washed twice with a 10% aqueous solution of sodium bicarbonate (100 cc in total). After decantation, the wash waters are extracted 3 times with methylene chloride (300 cc in total). The organic extracts are combined, dried over anhydrous sodium sulphate and concentrated to dryness under reduced pressure (20 mm Hg; 2.7 kPa) at 40° C. This gives a mixture of the two stereoisomeric forms of 2-(pyridin-3-yl)tetrahydrothiophen 1 -oxide (32.8 g). [Rf=0.36 and 0.40; chromatography on a thin layer of silica gel; solvent: ethyl acetate/methanol/water/acetic acid (75/20/5/5 by volume)].

2-(Pyridin-3-yl)tetrahydrothiophen can be prepared by the method described in the European Patent Application published under No. 0046417.

The present invention includes within its scope pharmaceutical compositions which comprise, as active ingredient, at least one compound of general formula (I) in association with any other pharmaceutically compatible product, which can be inert or physiologically active. The compositions according to the invention can be administered orally, parenterally or rectally.

Tablets, pills, powders (in particular in gelatine capsules or in cachets) or granules can be used as solid compositions for oral administration. In these compositions, the active product according to the invention is mixed with one or more inert diluents such as starch, cellulose, sucrose, lactose or silica. These compositions can also comprise substances other than diluents, e.g. one or more lubricants such as magnesium stearate or talc, a colorant, a coating (coated tablets) or a varnish.

Liquid compositions for oral administration include pharmaceutically acceptable solutions, suspensions, emulsions, syrups and elixirs containing inert diluents such as water, ethanol, glycerol, vegetable oils or paraffin oil. These compositions can also comprise substances other than diluents, e.g. wetting, sweetening, thickening, flavouring or stabilising products.

Compositions for parenteral administration include sterile aqueous or non-aqueous solutions, suspensions or emulsions. Water, propylene glycol, a polyethylene glycol, vegetable oils, in particular olive oil, injectable organic esters, e.g. ethyl oleate, or other suitable organic solvents can be used as the solvent or vehicle. These composition may also contain adjuvants, in particular wetting, isotonicising, emulsifying, dispersing and stabilising agents. Sterilisation can be carried out in several ways, e.g. by filtration under aseptic conditions, by incorporating sterilising agents into the compositions, by irradiation or by heating. They can also be prepared in the form of sterile solid compositions which can be dissolved in an injectable sterile medium immediately before use.

Compositions for rectal administration are suppositories or rectal capsules, which, in addition to the active product, contain excipients such as cacao butter, semi-synthetic glycerides or polyethylene glycols.

In human therapy, the compounds of the invention are particularly useful in the treatment of hypertension. The doses depend on the desired effect and the duration of the treatment; for an adult, they are generally between 5 and 1000 mg per day, administered orally in one or more dosage units.

In general, the physician will determine the dosage which he considers to be most appropriate taking into account the age, the weight and other factors intrinsic to the patient to be treated.

The following examples illustrate pharmaceutical compositions according to the invention.

EXAMPLE 10

Tablets containing 25 mg doses of active product and having the following composition are prepared by the usual technique:

| | |
|---|---|
| N—methyl-2-(pyridin-3-yl)tetrahydrothiopyran-2-carbothioamide 1-oxide, A form(the more polar product) | 25 mg |
| starch | 60 mg |
| colloidal silica | 50 mg |
| magnesium stearate | 2 mg |

EXAMPLE 11

Tablets containing 25 mg doses of active product and having the following composition are prepared by the usual technique:

| | |
|---|---|
| N—methyl-2-(quinolin-3-yl)tetrahydrothiopyran-2-carbothioamide 1-oxide | 25 mg |
| starch | 60 mg |
| colloidal silica | 50 mg |
| magnesium stearate | 2 mg |

We claim:

1. A thioformamide derivative of the formula

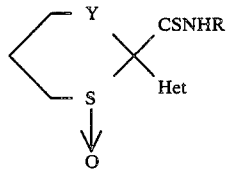

wherein R represents a hydrogen atom or an alkyl radical of 1 through 4 carbon atoms, Het represents quinolin-3-yl, and Y represents a valency bond or a methylene radical.

2. A thioformamide derivative according to claim 1 wherein R represents an alkyl radical of 1 through 3 carbon atoms, Het represents quinolin-3-yl, and Y represents a methylene radical.

3. A thioformamide derivative according to claim 1 wherein R represents a methyl or ethyl radical.

4. A thioformamide derivative according to claim 1 which is N-methyl-2-(quinolin-3-yl)tetrahydrothiopyran-2-carbothioamide 1-oxide.

5. A pharmaceutical composition for administration to a patient with hypertension which comprises, as active ingredient, an effective amount of a thioformamide derivative of the formula depicted in claim 1, wherein R, Het and Y are as defined in claim 1, in association with one or more compatible and pharmaceutically acceptable carriers or adjuvants.

6. A method for the treatment of a patient with hypertension which comprises administering to the patient in need of said treatment an effective amount of a thioformamide derivative as claimed in claim 1 sufficient to ameliorate the condition of the patient.

* * * * *